United States Patent
Lee et al.

(10) Patent No.: US 10,669,517 B2
(45) Date of Patent: Jun. 2, 2020

(54) APPARATUS FOR ACCELERATING REPRODUCTION OF ODOR FROM AIR-CONDITIONER AND METHOD FOR THE SAME

(71) Applicants: HYUNDAI MOTOR COMPANY, Seoul (KR); KIA MOTORS CORPORATION, Seoul (KR)

(72) Inventors: Tae Hee Lee, Hwaseong-si (KR); Ki Young Yoon, Seoul (KR); Jae Sik Choi, Suwon-si (KR); Ji Wan Kim, Yongin-si (KR); So Yoon Park, Seoul (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 0 days.

(21) Appl. No.: 16/230,869

(22) Filed: Dec. 21, 2018

(65) Prior Publication Data

US 2019/0119625 A1 Apr. 25, 2019

Related U.S. Application Data

(62) Division of application No. 14/931,840, filed on Nov. 3, 2015, now Pat. No. 10,202,573.

(30) Foreign Application Priority Data

Dec. 11, 2014 (KR) .................. 10-2014-0178113

(51) Int. Cl.
    *C12M 1/00* (2006.01)
    *C12M 1/12* (2006.01)
    (Continued)

(52) U.S. Cl.
    CPC .......... *C12M 41/14* (2013.01); *B60H 3/0085* (2013.01); *C12M 25/00* (2013.01); *C12M 29/24* (2013.01);
    (Continued)

(58) Field of Classification Search
    CPC ...... C12M 41/14; C12M 25/00; C12M 29/24; C12M 41/12; C12M 41/18; C12M 41/34;
    (Continued)

(56) References Cited

U.S. PATENT DOCUMENTS 6,629,420 B2   10/2003   Renders
2004/0141875 A1   7/2004   Doshi
(Continued)

FOREIGN PATENT DOCUMENTS

DE   4341467 A1   6/1995
DE   19608834 C1   9/1997
(Continued)

OTHER PUBLICATIONS

Machine Translation KR20120020309 to Lee; accessed Mar. 31, 2017 (Year: 2017).*
(Continued)

*Primary Examiner* — William H. Beisner
*Assistant Examiner* — Danielle B Henkel
(74) *Attorney, Agent, or Firm* — Morgan, Lewis & Bockius LLP

(57) ABSTRACT

The present invention relates to an apparatus and a method that can accelerate reproduction of odor from an air-conditioner by segmenting microorganisms, a temperature/humidity condition and nutrients for metabolism of the microorganisms as conditions for reproducing the odor from the air-conditioner and setting the segmented microorganisms, a
(Continued)

temperature/humidity condition and nutrients for metabolism of the microorganisms according to an accelerated condition thereof.

6 Claims, 7 Drawing Sheets

(51) Int. Cl.
- *C12M 1/02* (2006.01)
- *C12M 1/36* (2006.01)
- *B60H 3/00* (2006.01)
- *C12M 1/34* (2006.01)

(52) U.S. Cl.
CPC ............ *C12M 41/12* (2013.01); *C12M 41/18* (2013.01); *C12M 41/34* (2013.01); *C12M 41/48* (2013.01)

(58) Field of Classification Search
CPC ........ C12M 41/48; B60H 3/0085; C12N 1/14; C12N 1/20
See application file for complete search history.

(56) References Cited

U.S. PATENT DOCUMENTS

| | | |
|---|---|---|
| 2009/0032216 A1 | 2/2009 | Kim et al. |
| 2011/0079462 A1 | 4/2011 | Furuya et al. |

FOREIGN PATENT DOCUMENTS

| | | |
|---|---|---|
| DE | 102011100093 A1 | 10/2012 |
| JP | H02-013819 A | 1/1990 |
| JP | H06-000078 A | 1/1994 |
| JP | H10-185904 A | 7/1998 |
| JP | 2004-309455 A | 11/2004 |
| JP | 2006-345704 A | 12/2006 |
| JP | 2010-083220 A | 4/2010 |
| JP | 2013-024659 A | 2/2013 |
| KR | 10-1998-016080 | 5/1998 |
| KR | 10-2005-0103830 A | 11/2005 |
| KR | 10-2007-0007441 A | 1/2007 |
| KR | 10-0726005 B1 | 6/2007 |
| KR | 10-2008-0009668 A | 1/2008 |
| KR | 10-0854132 B1 | 8/2008 |
| KR | 10-2008-0080647 A | 9/2008 |
| KR | 10-2012-0020309 A | 3/2012 |
| KR | 2012-0020309 A | 3/2012 |
| KR | 10-1361394 B1 | 2/2014 |
| KR | 10-2014-0039867 A | 4/2014 |
| KR | 10-2014-0039882 A | 4/2014 |
| KR | 10-2014-0063314 A | 5/2014 |
| KR | 10-2014-0070699 A | 6/2014 |
| KR | 10-2014-0087537 A | 7/2014 |
| KR | 10-2014-0087538 A | 7/2014 |
| KR | 10-2014-0087539 A | 7/2014 |
| WO | 1996/036863 A1 | 11/1996 |
| WO | 2014/098543 A1 | 6/2014 |

OTHER PUBLICATIONS

English Abstract of JP2010-083220 (Year: 2010).*
Non-Final Office Action issued in U.S. App. No. 14/931,840, dated Apr. 18, 2017.
Final Office Action issued in U.S. App. No. 14/931,840, dated Oct. 23, 2017.
Non-Final Office Action issued in U.S. App. No. 14/931,840, dated Feb. 15, 2018.
Notice of Allowance issued in U.S. App. No. 14/931,840, dated Sep. 28, 2018.
L. H. Green, "Culturing and Preserving Microorganisms," Practical Handbook of Microbiology, 2nd Edition, CrC Press Inc, 2008, Chapter 3, pp. 31 to 36.
C. H. Collins, et al., "In Vitro Cultivation of Bacteria," Microbiological Methods, 5th Edition, Butterworth & Co Ltd., 1984, Chapters 4 and 5, pp. 56 to 96—ISBN 0-408-70957-X.

* cited by examiner

APPARATUS FOR ACCELERATING REPRODUCTION OF ODOR FROM AIR-CONDITIONER AND METHOD FOR THE SAME

CROSS-REFERENCE TO RELATED APPLICATION

This application is the Divisional application of U.S. patent application Ser. No. 14/931,840, filed on Nov. 3, 2015, now U.S. Pat. No. 10,202,573, which in turn claims priority under 35 U.S.C. § 119(a) to and the benefit of Korean Patent Application No. 10-2014-0178113 filed on Dec. 11, 2014 with the Korean Intellectual Property Office, the entire contents of which are incorporated herein by reference.

TECHNICAL FIELD

The present disclosure relates to an apparatus for accelerating reproduction of odor from an air-conditioner and a method for the same, and more particularly, to an apparatus for accelerating reproduction of odor from an air-conditioner and a method for the same which enable a bio-film to be generated within a short time in order to enhance the odor from the air-conditioner.

BACKGROUND

In general, when an air-conditioner of a vehicle is turned off while the vehicle is operated, bacteria are propagated in an evaporator due to moisture that remains in the evaporator, and as a result, mold and bacteria that are parasitized in the evaporator are discharged along with air at the time of turning on the air-conditioner. Thus, mold and bacteria may be absorbed by respiratory organs of a driver and a passenger and cause unpleasant smell.

As related art for removing odor from an air-conditioner, Korean Patent Unexamined Publication No. 10-2005-103830 (hereinafter, 'Document 1') is provided.

Document 1 discloses a method for removing smell of an air-conditioner which can remove moisture of an evaporator by further actuating a blow fan even after stopping while operating the air-conditioner in order to dry and remove the moisture of the evaporator.

Similarly, Korean Patent Registration No. 10-726225 (hereinafter, 'Document 2') discloses a smell removing method of an air conditioner for a car which can dry moisture that remains in an evaporator by actuating a blow fan.

However, the schemes presented in Documents 1 and 2 are less effect to remove the moisture of the evaporator by actuating the blow fan, since the fan continuously rotates even after the air conditioner stops, and as a result, a misrecognition problem as malfunction and deterioration of fuel efficiency may occur. Therefore, Documents 1 and 2 cannot be a fundamental countermeasure for removing the odor of the air-conditioner.

Meanwhile, as the life-span of a vehicle, a kind of bio film layer is formed while microorganisms causing the odor are adsorbed on the surface of the evaporator simultaneously when components of an air-conditioner system is decrepit and it is known that the microorganisms forming the bio film layer causes the odor.

Therefore, in recent years, technology has been developed to remove the odor form the air-conditioner by using the microorganism causing the odor from the air-conditioner and by using microorganisms not causing the odor.

However, there is a problem that an evaporator core mounted on the vehicle will be acceleratively worn out to the level of a used car (approximately 3 years or more) for an experiment for fundamentally removing the odor from the air-conditioner by using the microorganisms.

By considering that there is a tendency in which a R&D period of a new car which is newly released is shortened and design components applied for each new car are continuously changed, technology that can reproduce the odor of the air-conditioner within a short time is particularly required.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

The present invention has been made in an effort to provide an apparatus for accelerating reproduction of odor from an air-conditioner and a method for the same which operate an air-conditioner system for a vehicle under a practical operating condition and rapidly accelerate and reproduce and generate a bio film layer on the surface of an evaporator core to the level of a used car to accurately perform an air-conditioner odor removal reproduction experiment using microorganisms.

In one aspect, the present invention provides an apparatus for accelerating reproduction of odor from an air-conditioner including: a detachable microorganism inoculation unit; and a nutrient supply unit supplying nutrients to microorganisms inoculated in the microorganism inoculation unit.

In a preferred embodiment, the apparatus may further include a sample mounting unit for mounting the microorganism inoculation unit on a movement route of the nutrients supplied from the nutrient supply unit.

In another preferred embodiment, the apparatus may further include an air supply and temperature/humidity controller configured to circulate and supply air of which temperature and humidity are controlled to the microorganism inoculation unit.

In still another preferred embodiment, the nutrient supply unit may supply at least one selected from the group consisting of downtown air contaminants, exhaust gas, gasoline, diesel, and VOCs to the microorganism inoculation unit.

In yet another preferred embodiment, the microorganism inoculation unit may be an evaporator core.

In still yet another preferred embodiment, the microorganism inoculation unit may be the evaporator core and the sample mounting unit may include a sample jig unit including a jig housing forming a pipe connected with the air supply and temperature/humidity controller so as to form a circulation loop in which air supplied from the air supply and temperature/humidity controller returns to the air supply and temperature/humidity controller by passing through the evaporator core.

In still yet another preferred embodiment, the sample jig unit may further include an air blower mounted at a rear end of the evaporator core in the jig housing.

In still yet another preferred embodiment, the sample jig unit may further include a rectification lattice mounted at an inlet of an evaporator core in a jig housing; a second temperature/humidity sensor mounted at an outlet of the evaporator core; a relative hygrometer connected to a lower end of the evaporator core; and an airflow meter mounted at an outlet of a connection pipe connecting an outlet of the air blower and an upper chamber.

In still yet another preferred embodiment, a collection hole having a form in which one end of the jig housing is opened may be formed in the sample jig unit to collect odor passing through the evaporator core.

In still yet another preferred embodiment, the microorganism inoculation unit may be the evaporator core, and the air supply and temperature/humidity controller may further include a temperature/humidity controller for controlling the temperature of the air supplied to the sample mounting unit.

In still yet another preferred embodiment, the apparatus may further include: a chiller refrigeration unit for supplying cooling water to the evaporator core; and an electronic controller mounted at one side in the chamber casing to control the sample jig unit and the chiller refrigeration unit including the temperature/humidity controller under a desired operating condition.

In still yet another preferred embodiment, the temperature/humidity controller may include a supply air refrigeration unit including a cooling coil; a heater and a humidifying nozzle sequentially mounted above the cooling coil of the supply air refrigeration unit; a room blower mounted above the humidifying nozzle to discharge the air passing through the cooling coil and supply the discharged air to the sample jig unit; and a first temperature/humidity sensor mounted in an inner part adjacent to the sample jig unit.

In still yet another preferred embodiment, the apparatus may further include a collection unit collecting microorganisms to inoculate the microorganisms in the microorganism inoculation unit.

In still yet another preferred embodiment, the microorganism inoculation unit may be the evaporator core, and the collection unit may be configured in such a manner that the evaporator core is detachable and includes an evaporator core jig configured to guide floating microorganisms in the air and inoculate the guided microorganisms onto the evaporator core.

In still yet another preferred embodiment, the evaporator core jig may be configured to further include an air filter for filtering air.

In still yet another preferred embodiment, the evaporator core jig may include a case manufactured by a rectangular body having an inlet formed one surface and an outlet formed on the other surface and an inclination surface guiding air to the outlet formed on one surface corresponding to the inlet; a filter and core supporter mounted on a bottom surface in the case; an air filter mounted adjacent to the inlet above the filter and core supporter; and an evaporator core mounted adjacent to the outlet above the filter and core supporter.

In still yet another preferred embodiment, the evaporator core jig may include a case having an inclined suction plate with the inlet formed on a front surface thereof, the outlet formed on a rear surface thereof, and filter and core fixing plates having the same inclination angle as the inclined suction plate formed in line on both inner surfaces; and an air filter and an evaporator core mounted in line at the front and the rear on each filter and core fixing plate in the case.

In another aspect, the present invention provides a method for accelerating reproduction of odor from an air-conditioner including: collecting floating microorganisms in the air to inoculate the microorganisms in a microorganism inoculation unit; mounting and fixing the microorganism inoculation unit onto a sample mounting unit; and circulating and supplying air of which temperature and humidity are controlled to the microorganism inoculation unit together with nutrients while selectively operating a chiller refrigeration unit.

In a preferred embodiment, the method may further include collecting odor generated from a bio film layer generated in an evaporator core which is the microorganism inoculation unit.

In another preferred embodiment, the nutrients may be at least one selected from the group consisting of downtown air contaminants, exhaust gas, gasoline, diesel, and VOCs.

In still another preferred embodiment, in the circulating and supplying of the air of which temperature and humidity are controlled to the microorganism inoculation unit together with the nutrients, the temperature and the humidity may be constantly controlled by an air supply and temperature/humidity controller.

In yet another preferred embodiment, in the circulating and supplying of the air of which temperature and humidity are controlled to the microorganism inoculation unit together with the nutrients, a temperature/humidity mode in which the temperature and the humidity are constantly controlled by the air supply and temperature/humidity controller and a nutrient mode in which only the nutrients are supplied without controlling the temperature and the humidity may be alternately performed.

In still yet another preferred embodiment, an operation period and an idle period of the chiller refrigeration unit may be alternately performed according to a predetermined operating time rate.

In still yet another preferred embodiment, the microorganism inoculation unit may be the evaporator core.

Through the aforementioned problem solving means, the present invention provides the following effects.

According to the present invention, an air-conditioner system for a vehicle is operated under a practical operating condition and a bio film layer is rapidly accelerated and generated on the surface of an evaporator core to the level of a used car to accurately perform an air-conditioner odor removal reproduction experiment using microorganisms.

In particular, since multiple evaporator cores are mounted for each vehicle type and specification to variously generate the bio film layer on the surface of the evaporator core, an air-conditioner odor reproduction experiment can be performed under more accurate and various conditions.

Other aspects and preferred embodiments of the invention are discussed infra.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electronic vehicles, plug-in hybrid electronic vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electronic-powered vehicles.

BRIEF DESCRIPTION OF THE DRAWINGS

The above and other features of the present invention will now be described in detail with reference to certain exemplary embodiments thereof illustrated the accompanying drawings which are given hereinbelow by way of illustration only, and thus are not limitative of the present invention, and wherein.

Figure 1:
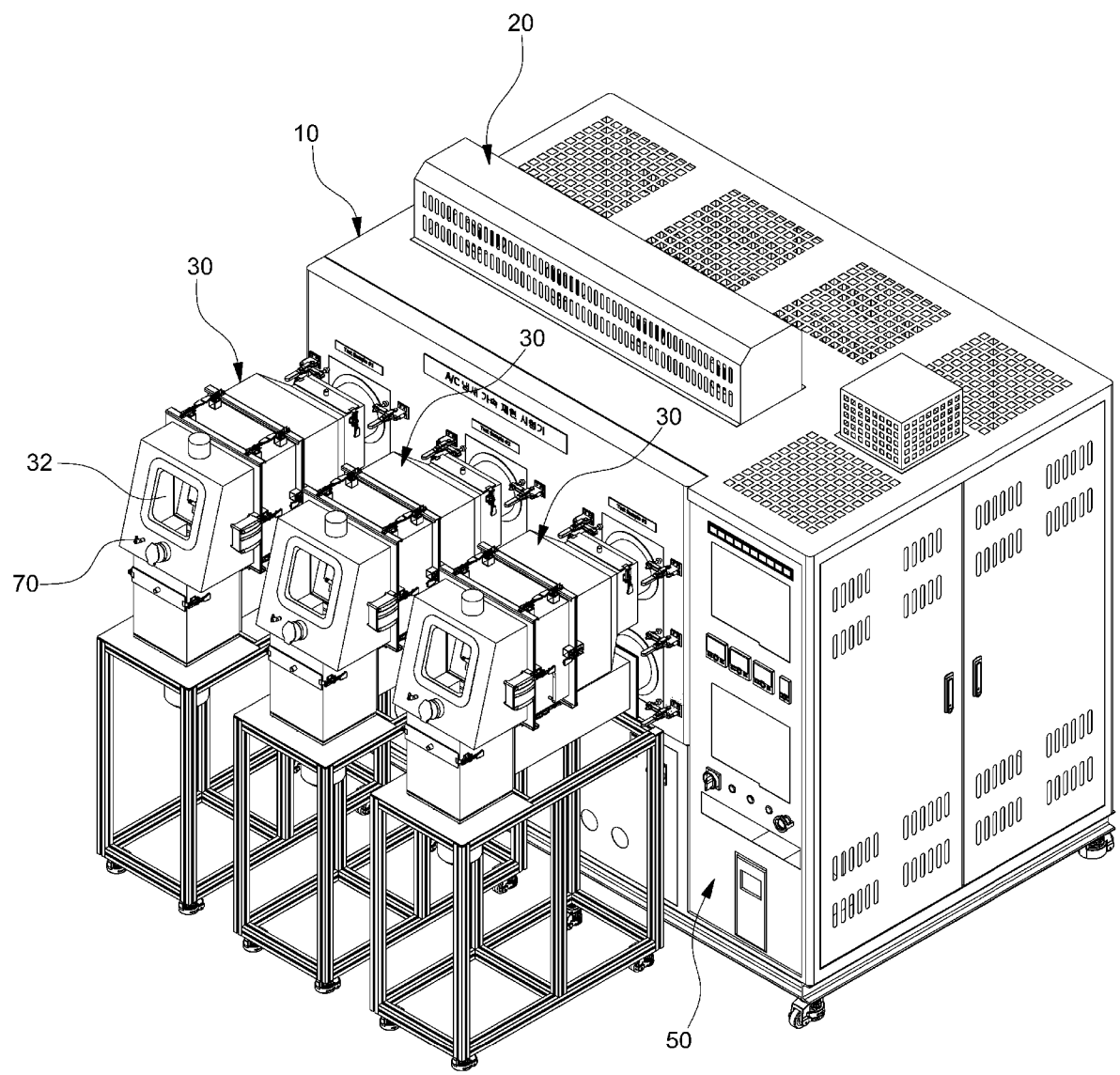
FIG. 1 is a perspective view illustrating an apparatus for accelerating reproduction of odor from an air-conditioner according to an embodiment of the present invention.
Figure 2:
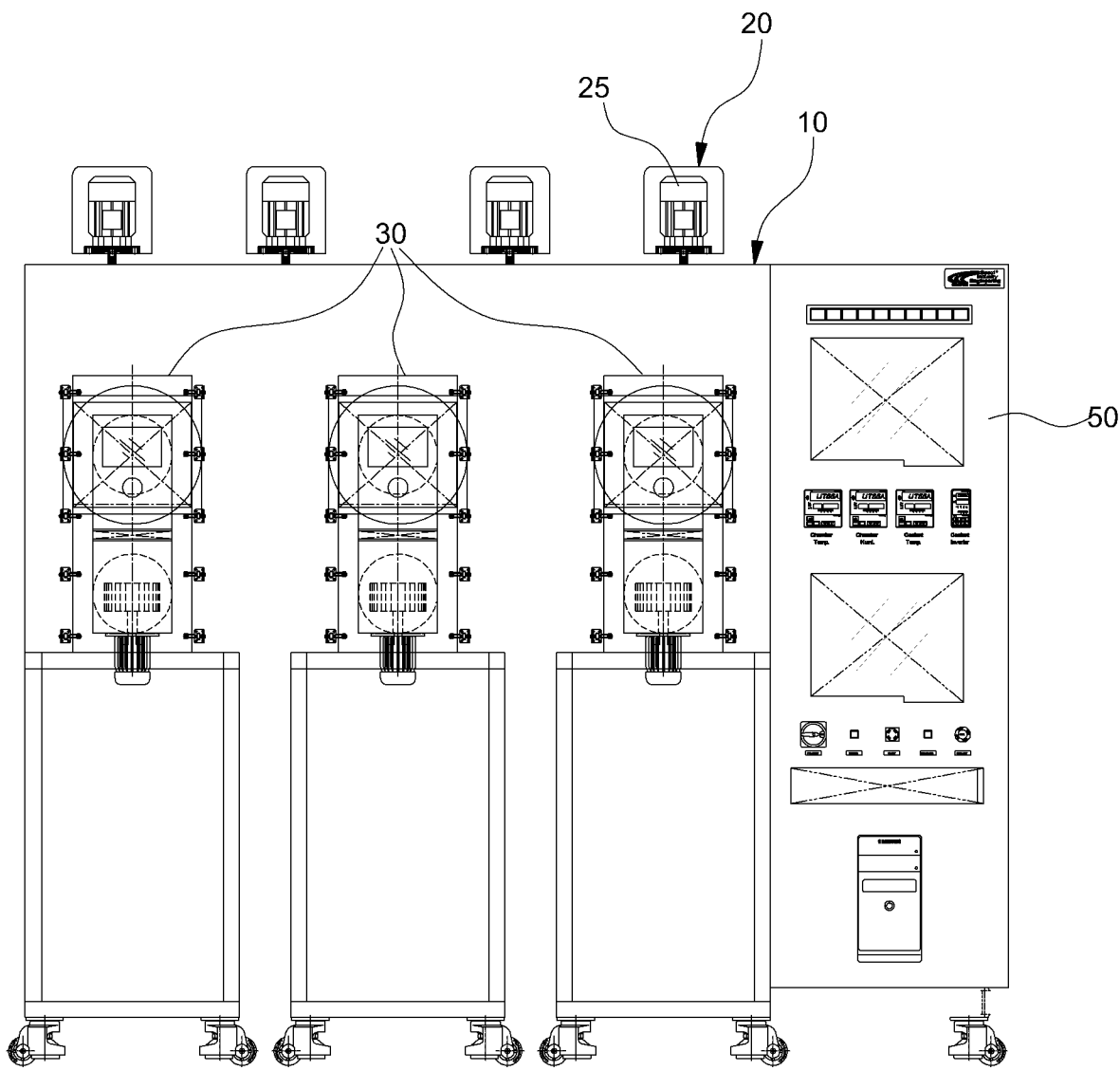
FIG. 2 is a front view illustrating the apparatus for accelerating reproduction of odor from an air-conditioner according to the embodiment of the present invention.
Figure 3:
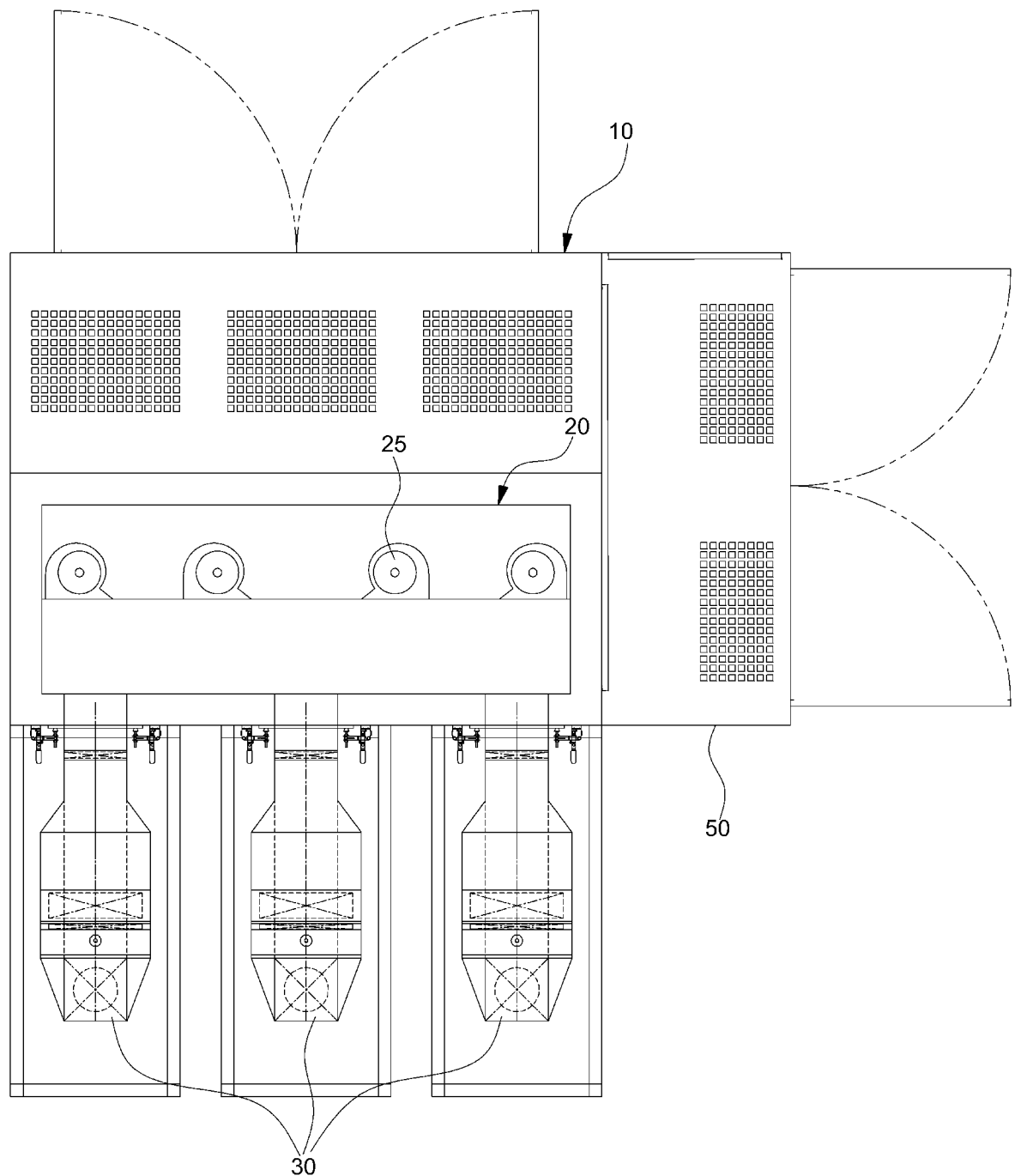
FIG. 3 is a plan view illustrating the apparatus for accelerating reproduction of odor from an air-conditioner according to the embodiment of the present invention.

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

A bio film layer among terms used in the present invention means a layer in which microorganisms which cause or do not cause odor are adsorbed on the surface of an evaporator core while an air-conditioner system operates.

The present invention places an emphasis on providing an apparatus for accelerating reproduction of odor from an air-conditioner that prescribes that the bio film layer formed by the microorganisms causes the odor from the air-conditioner, simulates an air-conditioner odor causing mechanism of a vehicle, and accelerates the simulation.

Further, the present invention has also been made in an effort to provide a method for accelerating reproduction of odor from an air-conditioner as a reproduction experiment apparatus designed to implement a method for reproducing odor from the air-conditioner which may reproduce the odor from the air-conditioner and configure a required environment that accelerates the reproduced odor.

The present invention relates to an apparatus and a method that can accelerate reproduction of odor from an air-conditioner by segmenting microorganisms, a temperature/humidity condition and nutrients for metabolism of the microorganisms as conditions for reproducing the odor from the air-conditioner and setting the segmented microorganisms, a temperature/humidity condition and nutrients for metabolism of the microorganisms according to an accelerated condition thereof.

In this regard, three components for reproducing the odor from the air-conditioner are segmented into the microorganisms in the atmosphere, an environmental condition (temperature/humidity) in a vehicle, and nutrients supplied for the metabolism.

By considering three components, in a preferred implementation example according to the present invention, three components for implementing an apparatus for accelerating reproduction of odor from an air-conditioner and a method for the same are set. This may be arranged by inoculation of the microorganisms, an air-conditioner operating time, and the number of stages of operating the air-conditioner (blower rpm).

It is necessary to implement an environment similar to the vehicle that causes odor for an experiment for accelerating reproduction of the odor from the air-conditioner. Therefore, the air-conditioner that simulates a vehicle air-conditioner system which causes a fundamental cause of generation of the odor may be adopted and whether to operate the air-conditioner and an operating time associated with an in-vehicle environmental condition, that is, the temperature and humidity conditions may be controlled. Further, in the present invention, the nutrients which the microorganisms metabolize are regarded as various contaminants in the air and the number of operating stages, that is, an air volume of a blower is designed to be controlled.

In particular, in the preferred implementation example of the present invention, the apparatus is configured to include a microorganism inoculation unit where the microorganisms are inoculated, a nutrient supply unit supplying the nutrients to the inoculated microorganisms, and an air supply and temperature/humidity controller that supplies air of which temperature/humidity is controlled in order to facilitate the metabolism of the microorganisms.

Further, in the preferred implementation example of the present invention, a configuration that reproduces an actual driving status to adsorb and collect the microorganisms in the evaporator corer is provided, while the microorganism inoculation unit (evaporator core) where the collected microorganisms are inoculated is configured to be mounted in the apparatus for accelerating reproduction of the odor from the air-conditioner.

Moreover, in the preferred implementation example of the present invention, the apparatus is configured to generate the bio film layer on the microorganism inoculation unit by implementing starting and stopping the air-conditioner using cooling water like actuality while controlling the temperature/humidity at which the microorganisms may grow and perform an odor reproduction mode under the accelerated condition.

Hereinafter, a preferred embodiment of the present invention will be described in more detail with reference to the accompanying drawings.

First, in order to collect the microorganisms in the atmospheric air introduced under an actual driving condition, not indoor air such as a laboratory, a collection unit for collecting the microorganisms is mounted on an actual vehicle, and as a result, the collection unit is adopted as a jig for the evaporator jig.

That is, in order to inoculate the floating microorganisms in the air, the jig for the evaporator core which may be mounted on the actual vehicle is provided to be fixed at a position such as a roof rack of the vehicle.

Figure 6:
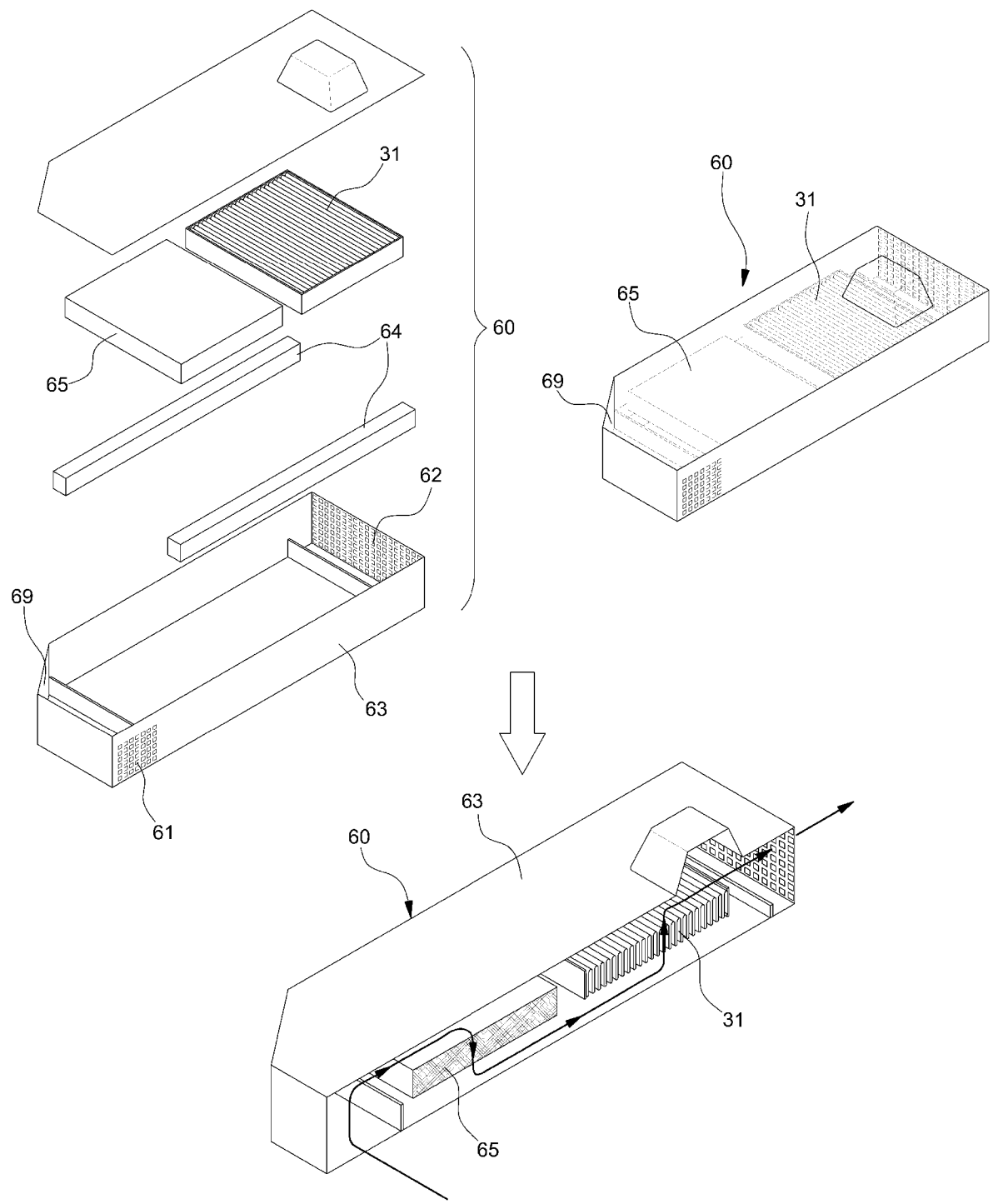
FIGS. 6 and 7 are diagrams each schematically illustrating an evaporator core jig which may be employed as the apparatus for accelerating reproduction of odor from an air-conditioner according to the embodiment of the present invention.

FIG. 6 is a diagram schematically illustrating an evaporator core jig which may be employed as an apparatus for accelerating reproduction of odor from an air-conditioner according to an embodiment of the present invention.

Referring to FIG. 6, a jig 60 for the evaporator core includes an inlet 61 formed at one side of a front surface, a rectangular case 63 with an outlet 62 used as a frame body on the other surface, and an inclination surface 69, which is inclined toward the outlet 62, formed at an opposite side to the inlet 61 through which air is introduced, that is, one side of a rear surface of the case 63 so as to guide the air to the outlet 62.

The jig 60 further includes a filter and core supporter 64 mounted on a bottom surface in the case 63, and an air filter 65 and an evaporator core 31 as a microorganism collection target fixed thereon. As a result, the air filter 65 is mounted adjacent to the inlet 61 on the filter and core supporter 64 and the evaporator core 31 is mounted adjacent to the outlet 62 on the filter and core supporter 64.

Therefore, when outdoor air enters through the inlet 61 of the case 63 mounted and fixed onto a roof rack, and the like while the vehicle is being driven, foreign substances are filtered by the air filter 65 and thereafter, the outdoor air is discharged to the outlet 62 by passing through the evaporator core 31, and as a result, the microorganisms are collected in the evaporator core 31 like a kind of seed.

The evaporator core in which the microorganisms are collected is mounted on the apparatus for accelerating reproduction of the odor from the air-conditioner to be described below to be used to accelerate reproduction of the odor from the air-conditioner.

Figure 7:
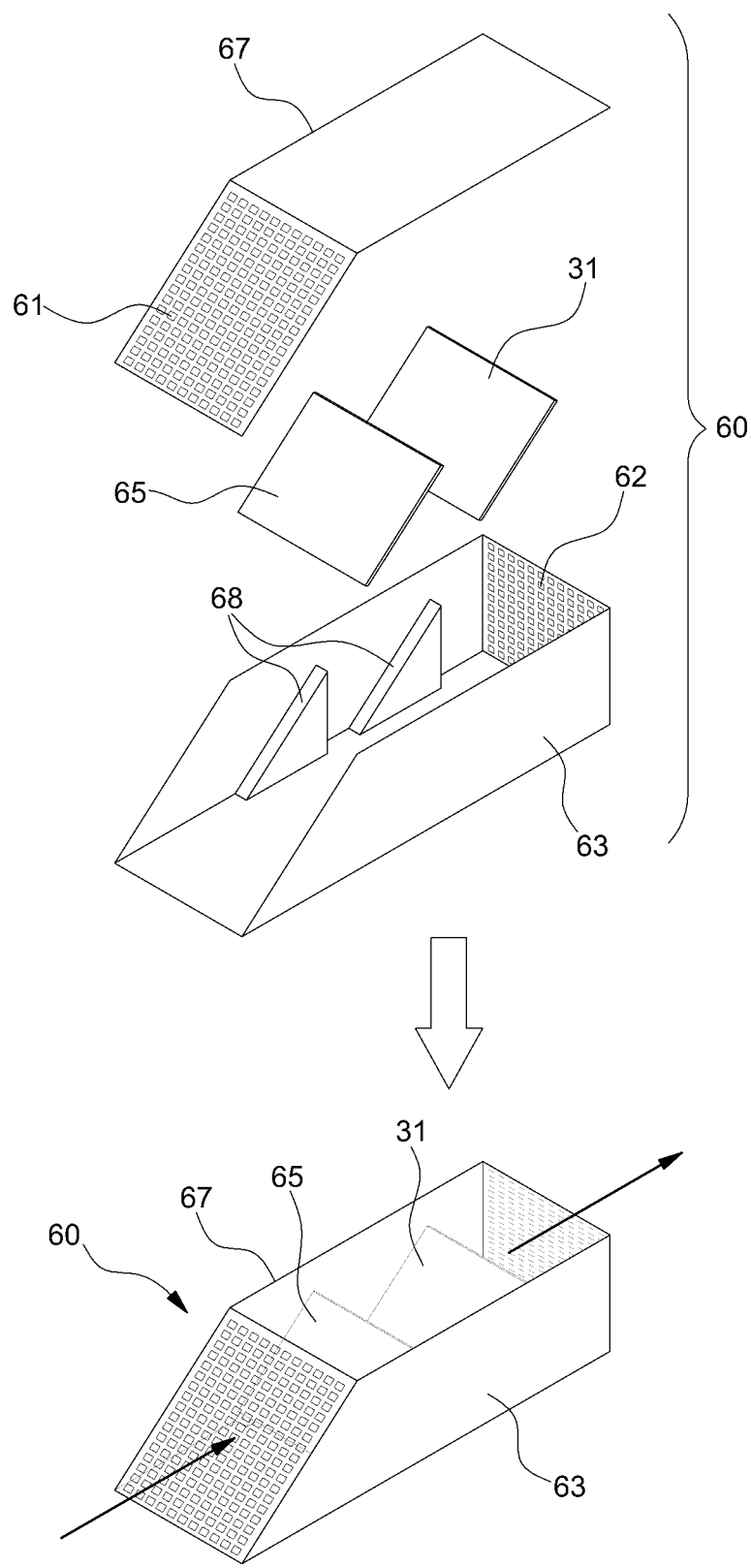

FIG. 7 is a diagram schematically illustrating another evaporator core jig which may be employed as an apparatus for accelerating reproduction of odor from an air-conditioner according to an embodiment of the present invention.

Referring to FIG. 7, a jig 60 for the evaporator core includes an inclined suction plate 67 with an inlet 61 formed on a front surface thereof, a case 63 with an outlet 62 as a frame body, which is formed on a rear surface thereof, and filter and core fixing plates 68 having the same inclination angle as the inclined suction plate 67 on both walls therein.

In this case, an air filter 65 and an evaporator core 31 are held and fixed onto each filter and core fixing plate 68 in the case 63, and as a result, the air filter 65 is mounted and fixed on the filter and core fixing plate 68 adjacent to the inlet 61 and the evaporator core 31 is mounted and fixed onto the filter and core fixing plate 68 adjacent to the outlet 62.

Therefore, when outdoor air enters through the inlet 61 of the inclined suction plate 67 of the case 63 mounted and fixed onto the roof rack, and the like while the vehicle is being driven, foreign substances are filtered by the air filter 65 and thereafter, the outdoor air is discharged to the outlet 62 by passing through the evaporator core 31, and as a result, the microorganisms are collected in the evaporator core 31 like a kind of seed.

Hereinafter, the apparatus for accelerating reproduction of the odor from the air-conditioner that is configured to be mounted with the microorganism inoculation unit in which the microorganisms are collected, preferably, the evaporator core in order to reproduce the odor from the air-conditioner will be described.

The apparatus for accelerating reproduction of the odor from the air-conditioner is configured to form a bio film on the evaporator core through the microorganisms collected through the jig for the evaporator core and reproduce the odor from the air-conditioner as it is by a metabolism action of the formed bio film.

To this end, the apparatus for accelerating reproduction of the odor from the air-conditioner according to an embodiment of the present invention is configured to be mounted with the evaporator core in which the microorganisms are collected on a movement route of the nutrients supplied from a nutrient supply unit. In the mounted evaporator core, the nutrients are received, and as a result, a metabolism activity is achieved and the odor is configured to be caused in a similar environment to the vehicle.

In particular, according to an embodiment of the present invention, temperature and humidity conditions are configured to be maintained under the accelerated condition for the metabolism action of the microorganisms, while supplying at least one of downtown air contaminants, exhaust gas, and VOCs as the nutrients to the evaporator core which is the microorganism inoculation unit. Further, according to an embodiment of the present invention, gasoline having similar ingredients to the aforementioned nutrients that act to actually cause odor may be configured to be selected and supplied in order to continuously supply homogeneous nutrients.

Hereinafter, the configuration of the apparatus for accelerating reproduction of odor from the air-conditioner according to an embodiment of the present invention will be described in more detail with reference to FIGS. 1 to 5. FIG. 1 is a perspective view of the apparatus, FIG. 2 is a front view of the apparatus, FIG. 3 is a plan view of the apparatus, and FIGS. 4 and 5 are left and right side views of the apparatus.

The apparatus for accelerating reproduction of odor from the air-conditioner according to an embodiment of the present invention includes an air supply and temperature/humidity controller for controlling the environmental condition for the metabolism of the microorganisms, a nutrient supply unit 70 for supplying the nutrients to the microorganisms, and a sample mounting unit connected with the air supply and temperature/humidity controller.

The air supply and temperature/humidity controller is configured to circularize and supply outdoor air or indoor air to the evaporator core side as described in the actual vehicle and control temperature and humidity conditions of the supplied air.

In this case, the nutrients provided from the nutrient supply unit 70 are configured to be included in the supplied air. The nutrients may be at least one of the downtown air contaminants, the exhaust gas, the gasoline, diesel, and the VOCs and preferably the gasoline.

The odor of the microorganisms may vary depending on food and that the nutrients are required for the actual metabolism of the microorganisms needs to be accurately specified in order to implement the actual vehicle driving condition through the reproduction experiment. By considering it, in the implementation example, as the ingredients associated with the actual microorganism metabolism, the exhaust gas of the vehicle, substances in downtown contaminated air, and the VOCs generated from an interior of a new vehicle are prescribed and are basically supplied as the nutrients.

Standardized nutrients for continuously supplying constant nutrients are required in order to achieve repeated reproducibility of the experiment. Further, since repeated reproduction needs to end within a short time as possible, concentrated nutrients may be supplied.

By considering the points, according one embodiment of the present invention, standardized nutrient gas is prepared by using vapor of the concentrated gasoline or diesel as compared with the exhaust gas or atmospheric contaminants.

Table 1 given below as a result of drawing a calibration line with toluene and inversely calculating the concentrations of the gasoline and the diesel according to a slope of the calibration line shows the concentrations of the gasoline and the diesel as compared with toluene of 76.7 ppm.

TABLE 1

| Ingredient name | Slope | Sample area | | Concentration (ppm(V/V)) | |
|---|---|---|---|---|---|
| | | Gasoline | Diesel | Gasoline | Diesel |
| TVOC | 1758.19 | 107.180 | 16.957 | 60.96 | 9.64 |

As shown even in Table 1 given above, most preferably, the gasoline in which the concentration of the contaminants functioning as the nutrients is high is configured to be supplied as the standardized nutrient gas as compared with the diesel.

Further, the sample mounting unit is configured to mount the evaporator core in which the microorganisms are inoculated and air of which temperature/humidity is configured to flow to the mounted evaporator core to be implemented in a form to simulate a microorganism metabolism in the vehicle.

In this case, the evaporator core configures a part of a cooling loop like the vehicle.

The air supply and temperature/humidity controller will be described below, which generates the bio film layer in the microorganism inoculation unit by controlling the temperature and the humidity while circulating and supplying outdoor or indoor air in an actual vehicle status to the microorganism inoculation unit.

According to the present implementation example, the apparatus for accelerating reproduction of odor from an air-conditioner includes a chamber casing 10 having a predetermined volume and an inner part of the chamber casing 10 is segmented into an upper chamber 11 and a lower chamber 12.

The air supply and temperature/humidity controller is installed in the chamber casing 10. Preferably, the air supply and temperature/humidity controller may be configured to include a room blower 25 for supplying air to a sample jig unit 30 to be described below and a temperature/humidity controller 20 configured to control the temperature and the humidity of the supplied air.

Figure 4:
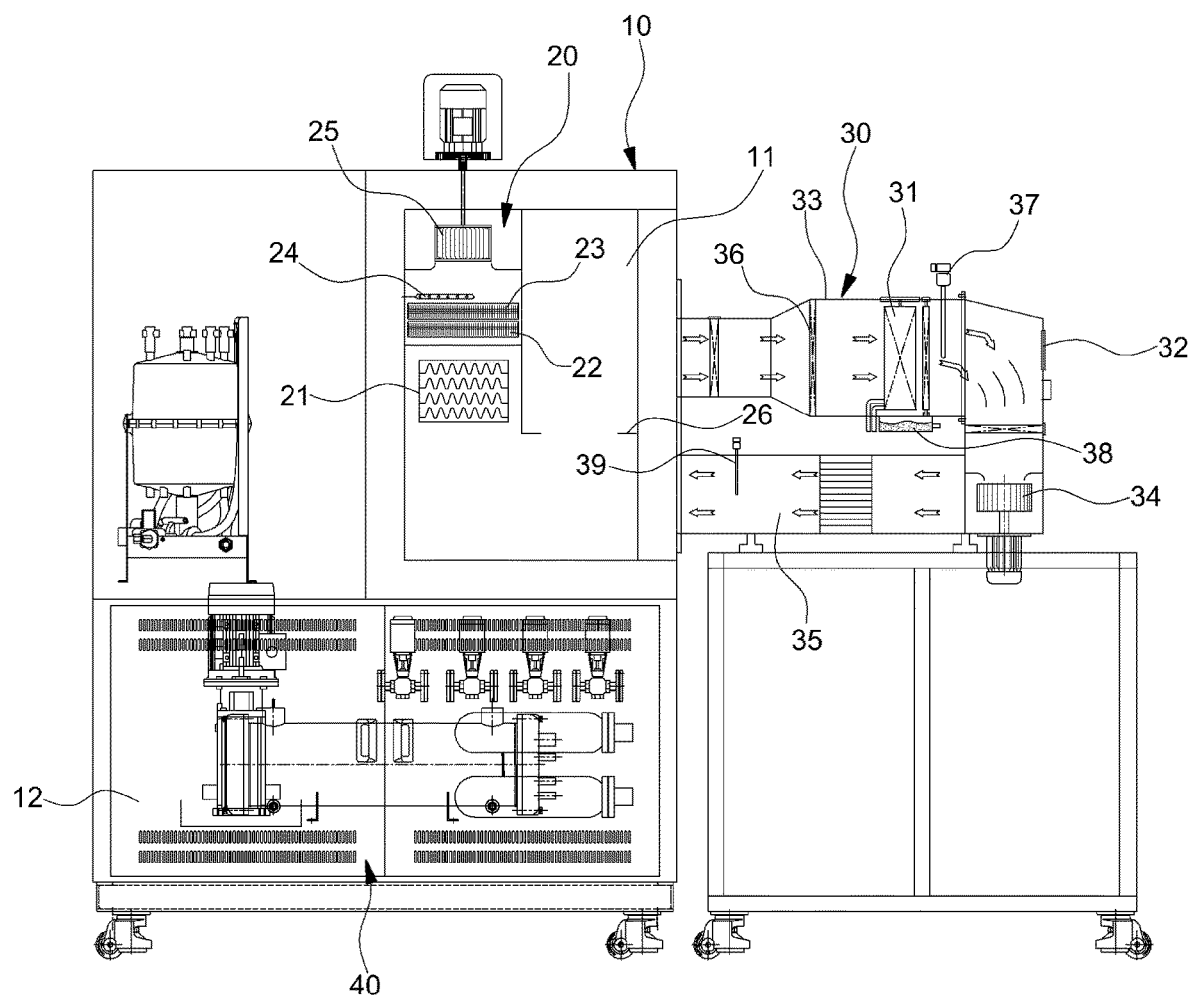
FIGS. 4 and 5 are a left side view and a right side view illustrating the apparatus for accelerating reproduction of odor from an air-conditioner according to the embodiment of the present invention.
Figure 5:
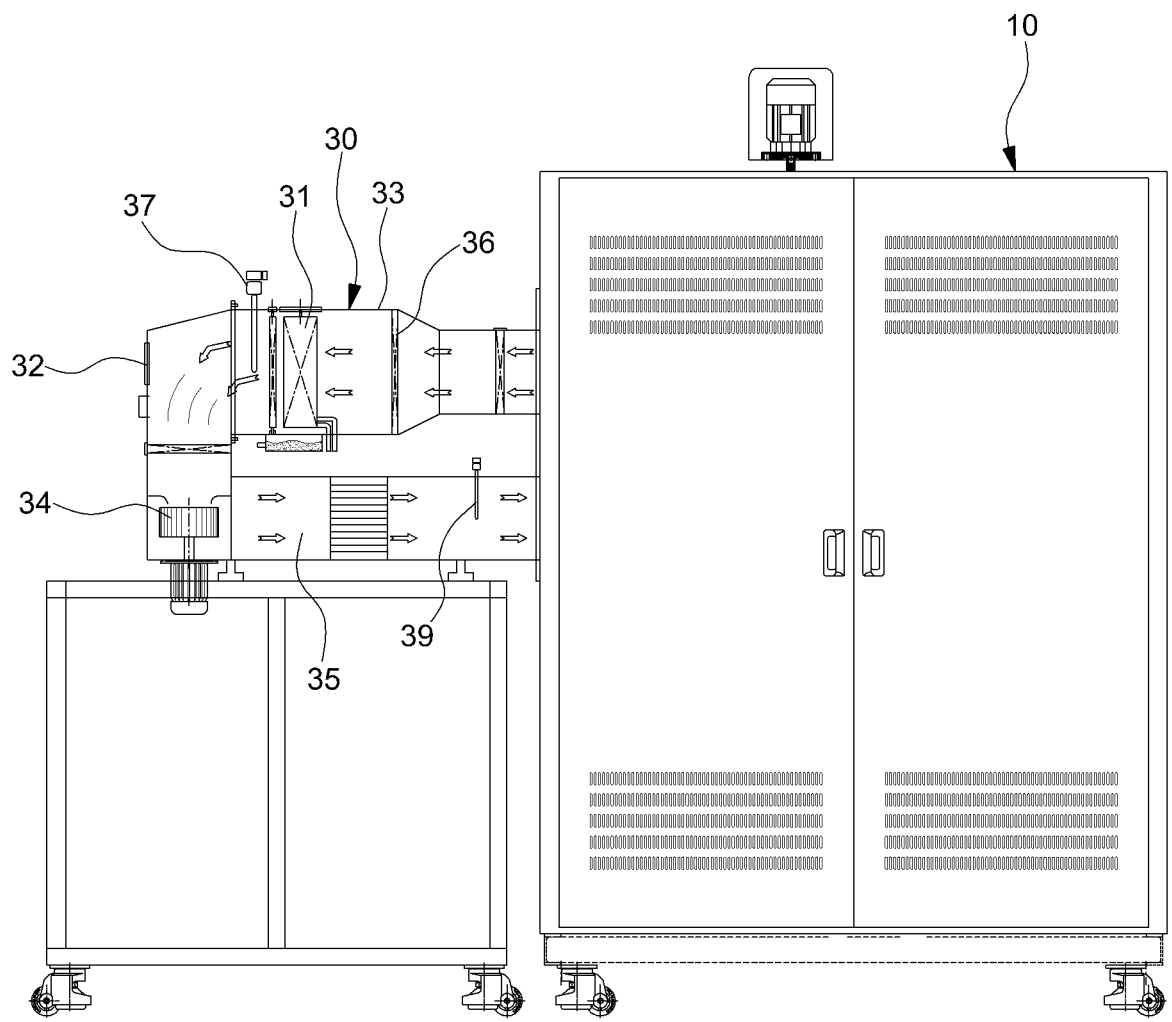

As illustrated in FIG. 4, the temperature/humidity controller 20 and the room blower 25 may be installed at one side of the upper chamber 11 of the chamber casing 10.

In detail, the temperature/humidity controller 20 includes a supply air refrigeration unit 21 configured to cool the temperature of the supplied air, a heater 23 mounted above a cooling coil 22 of the supply air refrigeration unit 21 to up-down control the temperature by heating the outdoor air or indoor air, and a humidifying nozzle 24 deployed above the heater 23 and connected with a humidifier, and the like in order to humidify discharged outdoor air or indoor air by passing through the heater from the supply air refrigeration unit 21.

Further, the room blower 25 is configured to be mounted above the humidifying nozzle 24 as illustrated in FIG. 4 to discharge the air passing through the cooling coil 22 and the heater 23 of the supply air refrigeration unit 21, and the humidifying nozzle 24 to the upper chamber 11 and supply the discharged air to the sample jig unit 30.

In this case, a first temperature/humidity sensor 26 that measures the temperature and the humidity of the air discharged from the supply air refrigeration unit 21 and transmits the measured temperature and humidity to an electronic controller 50 to be described below is mounted at an internal position of the upper chamber 11 adjacent to the sample jig unit 30.

Meanwhile, multiple sample jig units 30 on which the evaporator core 31 collecting the microorganisms is removably mounted are installed outside the upper chamber 11 of the chamber casing 10. Further, the chiller refrigeration unit 40 for circulating and supplying liquid cooling water to the evaporator core 31 is mounted in the lower chamber of the chamber casing 10.

The chiller refrigeration unit 40 is constituted by a general refrigeration unit including a cooling water cooler, a cooling water pump, a cooling water heater, a cooling refrigeration unit, and the like. In this case, the cooling water may be used as refrigerant unlike general air-conditioner refrigerant of an air-conditioner system.

Further, a humidifier that is connected with the humidifying nozzle of the upper chamber 11 of the chamber casing 10 to spray haze to the upper chamber may be deployed in the lower chamber 12 installed in which the chiller refrigeration unit 40 is installed.

Meanwhile, the evaporator core which is the microorganism inoculation unit is detachably configured in the apparatus for accelerating reproduction of odor from an air-conditioner through the sample mounting unit. That is, the microorganism inoculation unit is mounted on the evaporator core jig which is a collection unit to inoculate the collected microorganism and thereafter, removed from the collection unit and mounted in the sample mounting unit installed on a cooling roof simulating the air-conditioner.

The microorganism inoculation unit should not particularly be implemented to be detachably from the collection unit and the collection unit and the microorganism inoculation unit may be integrally configured. In this case, the collection unit and the microorganism inoculation unit which have an integrated structure may be directly mounted on the apparatus for accelerating reproduction of odor from an air-conditioner.

According to an embodiment of the present invention, the sample mounting unit is provided in the sample jig unit 30 for mounting and fixing the microorganism inoculation unit in the actual vehicle status.

The sample jig unit 30 is provided in a structure in which a collection hole 32 collecting odor from the air passing through the evaporator core 31 and a nutrient supply unit 70 for supplying the nutrients are formed, and as a result, the sample jig unit 30 has multiple jig housings 33 mounted on a front surface of the chamber casing 10, that is, outside a front surface of the upper chamber 11 as a frame body.

The reason why multiple jig housings 33 in which the evaporator core 31 is incorporated are deployed is that bio film layer generation experiments for different evaporator cores 31 may be simultaneously performed for each vehicle type or specification.

In particular, the evaporator core 31 is removably mounted in an intermediate part in the jig housing 33 to exchange heat with the air introduced from the air supply and temperature/humidity controller.

In this case, the evaporator core 31 may be removably mounted by applying a general assembly structure such as a slide scheme, a clamp scheme, a cover opening/closing scheme, and the like to the intermediate part of the jig housing 33.

Further, an air blower 34 for restoring the air introduced from the temperature/humidity controller 20, that is, the air passing through the evaporator core 31 toward the upper chamber again is mounted in the jig housing 33 and in addition, a connection pipe 35 is connected between an outlet of the air blower 34 and the upper chamber 11 so that the air passing through the evaporator core 31 is restored to the upper chamber 11.

Further, as another component of the sample jig unit 30, a rectification lattice 36 that rectifies the air that enters the evaporator core is mounted on an inlet of the evaporator core 31 in the jig housing 33.

In addition, the sample jig unit 30 includes a second temperature/humidity sensor 37 mounted on the outlet of the evaporator core 31, a relative hygrometer 38 connected to a lower end of the evaporator core 31, and an airflow meter 39 mounted on an outlet of the connection pipe 35 connecting an outlet of the air blower 34 and the upper chamber 11 as sensing means for changing a forming condition of the bio film layer by the microorganism and an odor reproduction condition.

In this case, the collection hole 32 for collecting odor in the air passing through the evaporator core 31 is penetratively formed on a front surface of the jig housing 33, that is, at a rear position of the evaporator core 31 to be openable/closable.

Moreover, a nutrient supply unit 70 for supplying the nutrients is formed on the jig housing and the nutrients are supplied with the microorganisms at the evaporator core side through the nutrient supply unit.

Meanwhile, an electronic controller 50 which is a kind of controller for controlling the room blower and the heater of the temperature/humidity controller 20, the air blower of the sample jig unit 30, a cooling pump and a cooler of the chiller refrigeration unit 40, and the like according to a desired operating condition is mounted at one side in the chamber casing 10 based on signals of various sensing means.

Herein, an operation flow of the apparatus for accelerating reproduction of odor from an air-conditioner, which includes the above configuration, will be described below.

Currently, since an air-conditioner odor reproduction experiment is provided, the air-conditioner odor may be applied in an actual vehicle.

Therefore, the present invention is characterized in that the bio film layer is configured to be acceleratively generated in the evaporator core through an operation depending on a cycle mode to which an actual vehicle monitoring is reflected and temperature/humidity control.

To this end, the method for accelerating reproduction odor from an air-conditioner is configured to include collecting the floating microorganisms in the air to inoculate the microorganisms in the microorganism inoculation unit, mounting and fixing the microorganisms inoculation unit onto the sample mounting unit, and circulating and supplying air of temperature and humidity are controlled to the microorganism inoculation unit together with the nutrients.

In detail, a process is preferentially performed, in which the microorganism inoculation unit is mounted on the microorganism inoculation unit having the structure illustrated in FIG. 6 and thereafter, the vehicle mounted with the collection unit is driven. Preferably, the collection unit may be mounted on the vehicle roof.

Such a process corresponds to a step in which the microorganisms in the atmosphere are introduced and collected in the evaporator core jig which is the collection unit and the collected microorganisms are inoculated on the microorganism inoculation unit in the collection unit. In this regard, the collection unit may be configured integrally with the microorganism inoculation unit and in this case, the experiment is performed by directly mounting the integral structure on the apparatus for accelerating reproduction of odor from an air-conditioner.

Next, the evaporator core corresponding to the microorganism inoculation unit is mounted on the apparatus for accelerating reproduction order from an air-conditioner manufactured for growth and a metabolic action of the microorganisms by using the sample mounting unit.

In this case, multiple sample jig units 30 are provided and multiple different evaporator cores 31 may be simultaneously deployed for each vehicle type or specification.

Next, a step is performed, in which outdoor or indoor air in an actual vehicle status is circulated and supplied to the microorganism inoculation unit and the temperature and the humidity are controlled to generate the microorganism inoculation unit on the bio film layer.

In this step, the supply air refrigeration unit 21 of the temperature/humidity controller 20 installed in the upper chamber 11 of the chamber casing 10 and the chiller refrigeration unit 40 installed in the lower chamber 12 are operated. In this case, the respective components are repeatedly operated and stopped under various environmental conditions in which the bio film layer by the microorganisms may be formed on the surface of the evaporator core 31.

Therefore, when the supply air refrigeration unit 21 such as an actual vehicular air-conditioner discharges the outdoor or indoor air while cooling the outdoor or indoor air, the discharged air flows to the evaporator core 31.

Refrigerant may be configured to be circulated while passing through the evaporator core 31 by operating the chiller refrigeration unit 40. The refrigerant may become liquid-state cooling water unlike general air-conditioner refrigerant of the air-conditioner system.

The refrigerant exchange heat with the air passing through the evaporator core 31 while being circulated and condensed water by the heat exchange is formed on the surface of the evaporator core 31.

Further, cooled air passing through the evaporator core 31 is subjected to repeated circulation in which the cooled air is restored to the upper chamber 11 through the connection pipe 35 and the restored air is suctioned by the room blower again to be discharged to the upper chamber again.

As the operational flow is repeated, the bio film layer depending on the growth of the microorganisms is generated on the surface of the evaporator core 31 in which the microorganisms are inoculated.

During such a process, an operating time of the refrigeration unit and the rpm of the room blower may be controlled according to a predetermined scheme.

For example, as the operating time of the refrigeration unit, an operation period and an idle period may be alternately set by considering a general scheme in which a driver in the actual vehicle operates the air-conditioner. Further, the rpm of the room blower may also be variably set according to the predetermined scheme.

Meanwhile, unlike this, in order to accelerate reproduction of odor, a condition in which the odor of the air-conditioner within a shortest time is determined and the operating time of the refrigeration unit and the rpm of the room blower are fixed according to the determined condition to operate the apparatus for accelerating reproduction of odor from an air-conditioner.

The resulting operating condition may be set as follows.

In the experimental example, an air-conditioner operating model to be applied to the apparatus for accelerating reproduction odor from an air-conditioner is calculated by collecting a driving time of the actual vehicle and the operating time of the air-conditioner.

TABLE 2

| Segmentation | Spring | Summer | Autumn | Winter | One year |
|---|---|---|---|---|---|
| Vehicle 1 | 136.6 | 93.7 | 83.6 | 89.2 | 403.2 |
| Vehicle 2 | 138.6 | 129.7 | 110.7 | 98.9 | 477.8 |
| Vehicle 3 | 71.9 | 85.7 | 66.8 | 72.9 | 297.3 |
| Vehicle 4 | 126.6 | 73.7 | 104.1 | 120.0 | 424.3 |
| Vehicle 5 | 112.1 | 94.6 | 84.3 | 120.5 | 411.5 |
| Vehicle 6 | 64.7 | 100.6 | 51.3 | 143.7 | 429.2 |
| Average | 108.4 | 96.3 | 83.5 | 107.5 | 429.2 |

TABLE 3

| Segmentation | Spring | Summer | Autumn | Winter | One year |
|---|---|---|---|---|---|
| Vehicle 1 | 62.0 | 74.4 | 41.4 | 19.7 | 197.4 |
| Vehicle 2 | 54.4 | 107.0 | 83.2 | 15.0 | 259.7 |
| Vehicle 3 | 6.8 | 40.1 | 6.5 | 0.5 | 53.9 |
| Vehicle 4 | 6.6 | 30.2 | 10.7 | 0.4 | 47.9 |
| Vehicle 5 | 6.7 | 32.9 | 6.3 | 0.2 | 46.1 |
| Vehicle 6 | 2.1 | 35.3 | 17.6 | 0.3 | 55.4 |
| Average | 23.1 | 53.3 | 27.6 | 6.0 | 110.1 |

Table 2 shows the driving time for each vehicle and Table 3 shows the operating the air-conditioner in the corresponding vehicle.

In Table 4 given below, a converted air-conditioner operating rate for each season is calculated based on data of Tables 2 and 3.

In this regard, since operating patterns of spring and autumn show a similar result, the spring and the autumn are together classified in order to reduce an experimental unit.

TABLE 4

| Segmentation | Spring/autumn | Summer | Winter |
|---|---|---|---|
| Months | March to May and September to November | June to August | December to February |
| | 6 months | 3 months | 3 months |
| Total hours | 4,392 | 2,208 | 2,160 |
| Average driving time (A) | 192 | 96 | 108 |
| Average operating time (B) | 51 | 53 | 6 |
| Operating time ratio (C = B/A) | 26% | 55% | 6% |
| 8-hour driving reference (D = 8*C) | 2.1 | 4.4 | 0.4 |
| Operating time ratio | X(1.5 h) + Y(0.5 h) Repeated four times | X(0.9 h) + Y(1.1 h) Repeated four times | X(1.9 h) + Y(0.1 h) Repeated four times |

An average driving time is a driving time of each season in Table 2 and an average operating time is an air-conditioner operating time (the sum of the spring and the autumn in the case of the spring/autumn) of each season in Table 3.

The operating time rate is acquired by dividing the average operating time by the average driving time and an operating time when the vehicle is driven for 8 hours is represented as a 8-hour driving reference D.

The operating time rate C and the 8-hour driving reference operating time D are used to segment the simulated operating time of the air-conditioner into the operating period and the idle period.

For example, in the case of the spring/autumn, since the air-conditioner is operated for 2.1 hours with the 8-hour driving reference, the operating period of 2.1 hours and the idle period of 5.9 hours are set to be included.

Meanwhile, in order to reflect a driving condition in which the driving and parking of the vehicle and the on/off of the air-conditioner are repeated, the operating time rate is set so that the operating period and the idle period are repeated four times within 8 hours as one cycle.

Therefore, as shown at a lowermost end of Table 4, in the case of the spring/autumn, the idle period (1.5 h) and the operating period (0.5 h) are repeated four times. Similarly, in the case of summer, the idle period (0.9 h) and the operating period (1.1 h) are repeated four times and in case of winter, the idle period (1.9 h) and the operating period (0.1 h) are repeated four times.

A control factor rated with the operating time of the air-conditioner is set to 3 stages to be used for the experiment.

Moreover, in addition to the air-conditioner operating time, the temperature and the humidity conditions for each season and a condition regarding an air volume of the supplied outdoor air may be additionally set. In this case, the temperature and humidity conditions are set by considering a lowest temperature at which the metabolic activity of the microorganisms is available by considering average temperature and humidity of each season. Further, the outdoor air volume is segmented into three stages by considering the number of operating stages of the air-conditioner.

In this regard, the set conditions will be described below.

TABLE 5

| | Segmentation Control factors | | |
|---|---|---|---|
| Level | Temperature (humidity) | Operating time (air-conditioner) | Outdoor air volume (blower) |
| 1 | 13° C.(50%) | (1.9 + 0.1)h | 70 CMH |
| 2 | 23° C.(70%) | (1.5 + 0.5)h | 170 CMH |
| 3 | 33° C.(90%) | (0.9 + 1.1)h | 270 CMH |

As described above, an optimal model is calculated by appropriately combining three control factors.

In this case, in order to promote the growth and metabolism of the microorganism and implement air-conditioner odor similar to odor of the actual vehicle, a temperature/humidity mode and a nutrient mode are segmented to be performed each for 8 hours.

In the temperature/humidity mode, the air of which temperature and humidity are controlled and is a mode to drive the air-conditioner for a set operating time and the nutrient mode is a mode to drive the air-conditioner for a set operating time while supplying the nutrients.

TABLE 6

| | Segmentation | | | |
|---|---|---|---|---|
| | Control factor | | | Odor collection |
| Level | Temperature (humidity) | Operating time (air-conditioner) | Outdoor air volume (blower) | result Required time/strength |
| 1 | 13° C.(50%) | (1.9 + 0.1)h | 70 CMH | 92 h/1.9 (bad odor) |
| 2 | 13° C. (50%) | (1.5 + 0.5)h | 170 CMH | 92 h/2.1 (bad odor + poultry waste odor) |
| 3 | 13° C. (50%) | (0.9 + 1.1)h | 270 CMH | 92 h/1.9 (muddy odor + odor) |
| 4 | 23° C. (70%) | (1.9 + 0.1)h | 270 CMH | 144 h/2.7 |
| 5 | 23° C. (70%) | (1.5 + 0.5)h | 170 CMH | 144 h/3.0 |
| 6 | 23° C. (70%) | (0.9 + 1.1)h | 70 CMH | 144 h/3.1 |
| 7 | 33° C. (90%) | (1.9 + 0.1)h | 270 CMH | 68 h/3.0 (musty odor + burn odor) |
| 8 | 33° C. (90%) | (1.5 + 0.5)h | 70 CMH | 68 h/3.0 (spoiling odor + rag odor) |
| 9 | 33° C. (90%) | (0.9 + 1.1)h | 170 CMH | 68 h/3.0 (musty odor) |

As shown in Table 6, it may be verified the odor is rapidly generated 9-time experimental results and experimental conditions #7 to 9 and in particular, when musty odor and burn odor are accumulated, condition #8 may be adopted as the optimal condition by considering that the musty odor and the burn odor are switched to spoiling odor and rag odor.

By the condition adopted through such an experiment, the reproduction of the odor from the air-conditioner is accelerated by driving the apparatus for accelerating odor from an air-conditioner.

Therefore, according to the preferred implementation example of the present invention, generation of the bio film layer in the evaporator core 31 may be reproduced, the odor generated from the bio film layer generated in the evaporator core 31 may be collected through the collection hole 32 of the jig housing 33, and the collected odor may be used as data for determining which microorganism the collected odor is caused from.

That is, the odor collected through the bio film layer generated in the evaporator core 31 and the collection hole 32 is analyzed to distinguish the microorganisms causing the air-conditioner odor and the microorganisms not causing the odor, and as a result, a basis to fundamentally remove the air-conditioner odor may be constructed.

Meanwhile, the apparatus for accelerating reproduction of odor from an air-conditioner according to the present invention is used as technology that cleans up an air-conditioner odor problem of the new vehicle and analyzes a low-temperature concentration mechanism by the VOCs of the interior of the vehicle by together inputting the VOCs used in the vehicular interior into the evaporator core at the time of operating the air supply and temperature/humidity controller.

Although the present invention has been described with reference to the preferred embodiments, those skilled in the art will appreciate that various modifications and changes can be made, within the range without departing from the scope of the invention as disclosed in the accompanying claims. Further, a lot of changes of particular situations or materials can be made within the scope without departing from an essential area of the present invention. Therefore, the present invention is not limited to a detailed description of the preferred embodiments of the present invention and will include all embodiments within the appended claims.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. A method for accelerating reproduction of odor from an air-conditioner, the method comprising:
   collecting floating microorganisms in the air to inoculate the microorganisms in an evaporator core;
   mounting and fixing the evaporator core onto an evaporator core jig to inoculate the collected microorganisms thereonto;
   after the microorganisms are inoculated onto the evaporator core, detaching the evaporator core from the evaporator core jig and mounting the evaporator core to a sample jig; and
   circulating and supplying air of which temperature and humidity are controlled to the evaporator core together with nutrients while selectively operating the sample jig,
   wherein the evaporator core is configured to be detachable both from the evaporator core jig and from the sample jig.

2. The method of claim 1, further comprising:
   collecting odor generated from a bio film layer generated in the evaporator core.

3. The method of claim 1, wherein the nutrients are at least one selected from the group consisting of downtown air contaminants, exhaust gas, gasoline, diesel, and VOCs.

4. The method of claim 1, wherein:
   in the circulating and supplying of the air of which temperature and humidity are controlled to the evaporator core together with the nutrients, the temperature and the humidity are constantly controlled by an air supply and temperature/humidity controller.

5. The method of claim 1, wherein:
   in the circulating and supplying of the air of which temperature and humidity are controlled to the evaporator core together with the nutrients, a temperature/humidity mode in which the temperature and the humidity are constantly controlled by the air supply and temperature/humidity controller and a nutrient mode in which only the nutrients are supplied without controlling the temperature and the humidity are alternately performed.

6. The method of claim 1, wherein an operation period and an idle period of the sample jig are alternately performed according to a predetermined operating time rate.

* * * * *